(12) United States Patent
Baillon et al.

(10) Patent No.: US 7,427,398 B2
(45) Date of Patent: Sep. 23, 2008

(54) MAMMALIAN ANIMAL COMPOSITION

(75) Inventors: Marie-Louise Amanda Baillon, Leicestershire (GB); Richard Fulton Butterwick, Leicestershire (GB)

(73) Assignee: Mars, Inc., McLean, VA (US)

( * ) Notice: Subject to any disclaimer, the term of this patent is extended or adjusted under 35 U.S.C. 154(b) by 0 days.

(21) Appl. No.: 10/517,268

(22) PCT Filed: Jun. 6, 2003

(86) PCT No.: PCT/GB03/02469

§ 371 (c)(1),
(2), (4) Date: Oct. 25, 2005

(87) PCT Pub. No.: WO03/105596

PCT Pub. Date: Dec. 24, 2003

(65) Prior Publication Data

US 2006/0134082 A1 Jun. 22, 2006

(30) Foreign Application Priority Data

Jun. 6, 2002 (GB) .................................. 0212975.7

(51) Int. Cl.
*A61K 47/00* (2006.01)
*A01N 63/00* (2006.01)
*C12N 1/20* (2006.01)

(52) U.S. Cl. ................. 424/93.45; 424/439; 435/252.9; 435/854

(58) Field of Classification Search .................. None
See application file for complete search history.

(56) References Cited

U.S. PATENT DOCUMENTS 6,190,591 B1 2/2001 van Lengerich
6,461,607 B1 * 10/2002 Farmer .................... 424/93.45

FOREIGN PATENT DOCUMENTS

| EP | 0904784 | 3/1999 |
|---|---|---|
| WO | WO-9729645 | 8/1997 |
| WO | WO-9735596 | 10/1997 |
| WO | WO-0075284 | 12/2000 |
| WO | WO-0158465 | 8/2001 |
| WO | WO-0190311 | 11/2001 |
| WO | WO-0198516 | 12/2001 |
| WO | WO-0243649 | 6/2002 |
| WO | WO-02058712 | 8/2002 |

OTHER PUBLICATIONS

Rinkinen et al, "Interaction between Probiotic Lactic Acid Bacteria and Canine Enteric Pathogens: A Risk Factor for Intestinal Enterococcus Faecium Colonization?" Veterinary Microbiology 92 (2003), pp. 111-119.

Johnston et al, "An Unexpected Bacterial Florain the Proximal Small Intestineof Normal Cats," Veterinary Record (1993) 132, pp. 362-363.

* cited by examiner

*Primary Examiner*—David M. Naff
*Assistant Examiner*—Deborah K. Ware
(74) *Attorney, Agent, or Firm*—Fulbright & Jaworski LLP

(57) ABSTRACT

The present invention relates to the use of probiotic microorganism in the manufacture of a composition for the prevention or reduction of gastrointestinal *Campylobacter* infection in a mammalian animal. It also relates to a method for the prevention or reduction of gastrointestinal *Campylobacter* infection in a mammalian animal, the method comprising administering to said animal, a probiotic microorganism. The invention also relates to a probiotic microorganism, for use in preventing or reducing gastrointestinal *Campylobacter* infection in a mammalian animal.

6 Claims, 1 Drawing Sheet

MAMMALIAN ANIMAL COMPOSITION

CROSS-REFERENCE TO RELATED APPLICATIONS

This application is the National Stage Application of International Application PCT/GB03/02469 filed Jun. 6, 2003, which claims priority to Great Britain Application No. 0212975.7 filed Jun. 6, 2002.

TECHNICAL FIELD

The present invention relates to the use of a probiotic microorganism in the manufacture of a composition for the prevention or reduction of gastrointestinal *Campylobacter* infection in a mammalian animal. It also relates to a method for the prevention or reduction of gastrointestinal *Campylobacter* infection in a mammalian animal, the method comprising administering to said animal, a probiotic microorganism. The invention also relates to a probiotic microorganism, for use in preventing or reducing gastrointestinal *Campylobacter* infection in a mammalian animal.

BACKGROUND OF THE INVENTION

Companion animals, particularly dogs and cats, are significant vectors of non-food borne gastrointestinal infection. Decreasing the risk of infection of these animals, and the ability to reduce infection when it does occur plays an important role in reducing zoonotic risk. Zoonotic risk is the risk of transfer of infection from one species to another. Clearly, this includes the risk of transfer of infection from companion animals to humans.

In dogs and cats, *Campylobacter* and *E. coli* are the predominant gastrointestinal pathogens, causing both clinical and non-clinical infections.

In dogs and cats, fecal shedding of *Campylobacter* occurs in animals which are infected, whether clinical symptoms are shown or not.

*Campylobacter* is a most common zoonoses, as well as being a common cause of gastroenteritis in humans. It is estimated that 5% of all human *C. jejuni*-induced enteritis result from exposure to infected dogs or cats.

In view of the zoonotic risk of *Campylobacter* infection from companion animals to humans, it is recommended that control measures that should be considered, which include restricting contact of children with puppies which may be infected, pets which may be infected be kept away from food preparation areas, affected animals should be kept apart from healthy ones and thorough disinfecting of bedding, food bowls etc. should be carried out.

As mentioned above, *Campylobacter* infection in cats and dogs may or may not result in clinical symptoms. Thus it is difficult to know whether any animal, at any time, is infected or not. A 3 to 7 day incubation period is found in dogs and cats, which may be followed by a diarrhea that ranges from mild to transient to mucus laden bloody diarrhea. However, since diarrhea is symptomatic of an enormous number of problems, including a range of infections, dietary problems (rapid change, over eating, scavenging, food tolerance, food hypersensitivity), neoplasia, inflammatory bowel disease, pancreatitis, metabolic disease, systemic disease, and drug reactions, the noting of diarrhea in itself cannot be used to diagnose *Campylobacter* infection.

BRIEF SUMMARY OF THE INVENTION

Accordingly, it would be of benefit to provide means to reduce or prevent *Campylobacter* infection in the gastrointestinal tract, particularly of companion animals. A benefit is to reduce or prevent *Campylobacter* infection, without the need for a formal diagnosis of *Campylobacter* infection. A benefit of reducing or preventing *Campylobacter* infection in mammalian animals results in a reduction or prevention of shedding of *Campylobacter* in feces and thus reduces or prevents the zoonotic risk, particularly to humans.

Accordingly, the present invention provides the use of a probiotic microorganism in the manufacture of a composition for the prevention or reduction of gastrointestinal *Campylobacter* infection in a mammalian animal.

A probiotic microorganism is one which can help to promote a healthy intestinal tract. Probiotic microorganisms beneficially affect a host by improving the microbial balance.

The prevention or reduction of gastrointestinal *Campylobacter* infection results not only in a reduced presence of *Campylobacter* in the GI tract, but also, and importantly, reduces or prevents shedding of *Campylobacter* in feces. Reduction of the shedding of *Campylobacter* in feces is a significant factor in reducing or preventing the transfer of *Campylobacter* infection from animal to animal, including from companion animal to humans.

The probiotic microorganism may be any which is known, including one or more from the following:—

*Lactobacillus* (such as *murinus, ruminus, rhamnosis, acidophilus, reuteri* or *mucosae*), *Bifidobacterium, Bacterioides, Aostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weisella, Aerococcus, Oenococcus* and *Eubacterium*.

Typically, the *Campylobacter* infection will be *Campylobacter jejuni*. This is the most significant strain in humans which causes gastroenteritis. The *Campylobacter* infection may be any other, including *Campylobacter coli, C. upsaliensis, C. lari, C. fetus, C. rectus* and/or *C. hyointestinalis*.

The mammalian animal according to the present invention may be any. Preferably, the mammalian animal is a companion animal, such as the domestic dog or the domestic cat. In the present invention, the terms domestic dog and domestic cat mean dogs and cats, in particular *Felis domesticus* and *Canis domesticus*. The present invention also applies to humans.

The composition for the prevention or reduction of gastrointestinal *Campylobacter* infection may be any composition which a mammalian animal may take. Preferably it is a composition which any mammalian animal may consume in its diet. Thus, the invention covers standard food products as well as food snacks. The composition may comprise a cereal product or confectionery, such as snack bars, biscuits and sweet products, including candy and chocolate.

When the mammalian animal is a companion animal (a pet animal) the composition may encompass any product which a pet may consume, in particular in its diet. The composition is preferably a dry pet food. Such dry pet foods include dry kibbles comprising a cooked starch source.

The foodstuff may be a cooked product. It may incorporate meat or animal derived materials (such as beef, chicken, turkey, lamb, blood plasma, marrowbone etc. or two or more thereof). The composition may alternatively be meat-free (preferably including a meat substitute such as soya, maize gluten or a soya product). The composition may contain additional protein sources such as soya protein concentrate, milk proteins, gluten etc. The composition may contain a starch source such as one or more grains (e.g. wheat, corn, rice, oats, barley etc.) or may be starch-free. A typical dry commercial dog and cat food contains about 30% crude protein, about 10-20% fat and the remainder being carbohydrate, including dietary fiber and ash. A typical wet or moist product contains (on a dry matter basis) about 40% fat, 50% protein and the remainder being fiber and ash. The present invention is particularly relevant for a composition as hereindescribed which is sold as a diet, foodstuff or supplement for a cat or dog.

Further, the composition may be a foodstuff in the form of one or more of a cereal product, energy bar, breakfast cereal, confectionery, medicament, food supplement or a drink. The supplement may be in the form of a dried powder, tablet, capsule, liquid or gel.

The probiotic microorganism may be in any form, for example in a powdered dry form or in spore form (for the microorganisms which form spores). The probiotic may be encapsulated in order to protect it from moisture. In addition, the probiotic microorganism may have undergone processing in order for it to increase its survival in any processing. Accordingly, the microorganism may be coated or encapsulated in a polysaccharide, fat, starch, protein or in a sugar matrix. The probiotic microorganism may be in a coating (outer or a layer), or a filling, or it may be admixed throughout the composition.

It may be preferable to avoid the probiotic being in contact with flour as flour contains enzymes which may adversely affect the viability of the probiotic. Standard encapsulation techniques known in the art can be used, and for example, as discussed in U.S. Pat. No. 6,190,591 (which is incorporated by reference herein).

The composition according to the first aspect of the invention may comprise the probiotic microorganism in any concentration, preferably at a concentration of from $10^3$ to $10^{15}$ viable cells per gram of the total composition. This concentration of cells provides a suitable concentration for successful colonization of the gastrointestinal tract and providing the optimum health benefits to the animal. An additional probiotic strain may be present at a concentration of from $10^3$ to $10^{15}$ viable cells per gram of the total composition.

According to a second aspect, the present invention provides a method for the prevention or reduction of gastrointestinal *Campylobacter* infection in a mammalian animal, the method comprising the administration of a probiotic microorganism to said animal.

Preferably, the probiotic microorganism is comprised in a composition, for example as described above in relation to the first aspect of the invention.

All preferred features of the first aspect of the invention, also apply to the second.

In the method of the second aspect of the invention, the animal is preferably in need of the prevention or reduction of gastrointestinal *Campylobacter* infection.

The administration of the probiotic microorganism may be by any means or preferably the administration is oral administration (i.e. ingestion).

A third aspect of the present invention provides a probiotic microorganism for use in preventing or reducing gastrointestinal *Campylobacter* infection in a mammalian animal.

All preferred features of the first and second aspect of the invention, also apply to the third.

BRIEF DESCRIPTION OF THE DRAWINGS

The present invention is described with reference to the figures.

DETAILED DESCRIPTION OF THE INVENTION

Figure 1:
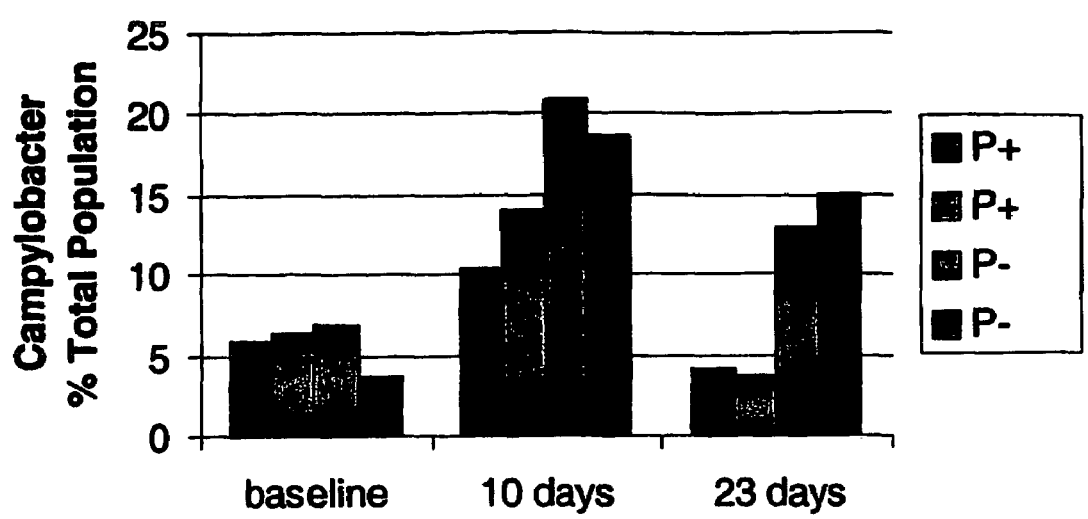
FIG. 1: Fecal bacteria counts by Fluorescent in-situ hybridization (FISH): *Campylobacter* as a % of total population. Showing post-antibiotic (baseline) levels compared to effect of probiotic+/− supplementation for 10 days or 23 days.

The present invention will now be described with reference to the following non-limiting examples:

EXAMPLE 1

Animal Details and Husbandry Conditions

Cats (n=48) housed in catcare 6 were selected for the study (table 1). Catcare 6 had recently been diagnosed with a clinical naturally acquired *Campylobacter* infection. The cats were group housed at all times and had constant access to fresh water.

Four rooms were selected to undergo probiotic+/− treatment.

In the 10 days prior to the beginning of the probiotic trial, all cats were treated with antibiotics to control the clinical *Campylobacter* infection. All cats received Ceporex (1 tablet twice daily for 10 days). Ceporex contains 50 mg cephalexin, a $3^{rd}$ generation cephalosporin antibiotic.

Feeding Regimen

All cats were group fed according to a standard protocol. Large trays of food containing 400 g/cat, being offered once daily at 2 pm and left down overnight. The diet was standard canned Whiskas Beef (chunk in loaf).

Probiotic Dosing Regimen

Cats in the probiotic+ treatment groups (rooms 1 and 2) were orally dosed with 10 mg ($1\times10^9$ cells) of a freeze-dried preparation of *Lactobacillus acidophilus*, deposited under with the International Depositary Authority, Aberdeen Scotland with Accession No. NCIMB 41117 on Nov. 13, 2001. The preparation was administered once daily after feeding, in a gelatin capsule. The probiotic− groups (rooms 11 and 12) received no capsule.

Dosing commenced immediately after the cessation of antibiotic therapy and continued for 27 days.

Study Design

The study was designed to incorporate measures at key points during the process of antibiotic treatment and recovery. The measures taken were:

Group daily food intakes.
Weekly bodyweight.
Group feces quality.
Bacterial counts by agar culture and FISH.
Bacterial profiling by API biochemical fingerprinting and ribotyping.

Methodology

Food Intakes

Daily food consumption was monitored for each room, being the amount offered minus that refused. Individual food intakes are not available for this study.

Feces Quality

Group feces quality was assessed daily using the Waltham Feces Scoring Guidelines™. Each defecation was graded on a subjective, 17 point scale. Individual feces scores are not available for this study.

Fecal Bacteria Profile

Feces voided overnight were discarded. Every defecation voided between 8 am and 4 pm was collected into a clean feces collection pot and used for bacteriological examination. Feces were processed immediately in the laboratory under appropriate incubation conditions.

The following bacterial groups were quantified using selective agars:
Anaerobic culture of *Lactobacilli* on MRSa agar (Oxoid)
Micro-aerobic culture of *Campylobacter* on selective agar (LabM)

In addition, the following bacterial groups were quantified by fluorescence in situ hybridization (FISH):
*Clostridia*
*Lactobacilli*
*Campylobacter*

Methodology for *Campylobacter* Enumeration Using Selective Agar

A swab of feces was spread onto a plate and incubated micro-aerobically (5% $O_2$), selecting for single colonies. This method is qualitative and does not provide quantitative information.

Statistical Analysis

Data were analyzed using multifactor ANOVA, with antioxidant supplementation+/− as the second factor and students t test, as appropriate. P<0.05 was considered significant.

Results

Fecal Bacteria

Plate Counts

*Lactobacilli* were enumerated on three occasions during the study:
towards the end of antibiotic therapy
following 10 days+/− probiotic treatment
following 23 days+/− probiotic treatment Total *Lactobacilli* in feces were enumerated using de Man, Rogosa, Sharpe (MRS) agar acidified to a pH of 5.0. There was no significant effect of probiotic treatment on absolute numbers of *Lactobacilli* at any time point.

*Campylobacter* were enumerated on four occasions during the study:
before the start of antibiotic therapy
towards the end of antibiotic therapy
following 10 days+/− probiotic treatment
following 23 days+/− probiotic treatment

TABLE 1

% of feces samples that tested positive for *Campylobacter* using selective agar.

| Campylobacter ($\log_{10}$) | Probiotic+ % positive | n | Probiotic− % positive | n |
|---|---|---|---|---|
| Pre-antibiotic | 100 | 12 | 100 | 12 |
| Post antibiotic | 50 | 12 | 67 | 12 |
| 10 days +/− probiotic | 67 | 12 | 100 | 11 |
| 23 days +/− probiotic | 88 | 17 | 100 | 15 |

This method is qualitative and merely indicates the presence or absence of *Campylobacter* in feces samples. Prior to antibiotic therapy, all feces samples cultured tested positive for *Campylobacter*, although this was decreased to 59% (overall) by antibiotic therapy. Following 10 days probiotic+/− supplementation, 100% of feces from the probiotic− group tested positive for *Campylobacter*, but this was decreased to 67% in the probiotic+ group. Following 23 days probiotic+/− supplementation, 100% of feces from the probiotic− group tested positive for *Campylobacter*, but this was decreased to 88% in the probiotic+ group (Table 1). Probiotic supplementation therefore decreased the prevalence of *Campylobacter* positive feces. Re-infection rates were also reduced in the probiotic+ group with 67% of fecal samples testing positive for *Campylobacter* ten days post treatment, compared to 100% of feces from the probiotic− group. These findings indicate strength resistance of healthy cats to infection with *Campylobacter* species following supplementation with *Lactobacilli acidophilus* (Accession No. NCIMB 41117).

Fluorescence in Situ Hybridization

Enumeration of *Clostridia*, *Lactobacilli* and *Campylobacter* by FISH was conducted on four occasions during the study:
before the start of antibiotic therapy
towards the end of antibiotic therapy
following 10 days+/− probiotic treatment
following 23 days+/− probiotic treatment Bacterial counts (% total population) are given in Table 2 for *Campylobacter* and shown graphically in FIG. 1.

There was no significant effect of probiotic supplementation on *Lactobacilli* as a % of the total population or absolute numbers ($\log_{10}$) at any time during the study.

There was a significant difference between probiotic+/− groups in Clostridia (as a % of the total population as well as a small (less than one $\log_{10}$) but significant (p=0.007) difference in absolute numbers) prior to the beginning of antibiotic therapy. This difference between groups was, however, eliminated by the antibiotic therapy such that at baseline both groups were similar. Administration of probiotics significantly decreased Clostridia (as % of total population) at both 10 and 23 days. This decrease was not reflected in absolute numbers of Clostridia, although at 23 days there was a small (less than one $\log_{10}$) although significant (p=0.006) difference between the probiotic+/− groups.

There was no difference in *Campylobacter* between the groups at baseline. At 10 days+/− probiotic supplementation, *Campylobacter* (as % total population) had increased in all 4 groups (FIG. 1). However, *Campylobacter* (as % of total population) was significantly reduced in probiotic treated animals compared to negative controls at 10 days (table 2, FIG. 1). Following 23 days probiotic supplementation *Campylobacter* (as % total population) was decreased compared to baseline, but was increased compared to baseline in those animals that did not receive probiotics. At 23 days *Campylobacter* (as % of total population) was significantly lower in probiotic treated animals compared to negative controls (table 2, FIG. 1). This was reflected in absolute numbers at 23 days, with a small (less than one $\log_{10}$) but significant difference between groups.

TABLE 2

Fecal bacteria counts by FISH: *Campylobacter* as a % of total population.

| Campylobacter | Probiotic+ | | | Probiotic− | | | Significance of difference |
|---|---|---|---|---|---|---|---|
| | mean | SD | n | mean | SD | n | |
| Pre-antibiotics | 14.27 | 4.92 | 11 | 14.48 | 4.15 | 10 | 0.727 |
| Post-antibiotics | 6.14 | 3.83 | 10 | 5.25 | 2.3 | 12 | 0.494 |

TABLE 2-continued

Fecal bacteria counts by FISH:
Campylobacter as a % of total population.

| Campylobacter | Probiotic+ | | | Probiotic− | | | Significance of difference |
|---|---|---|---|---|---|---|---|
| | mean | SD | n | mean | SD | n | |
| 10 days treatment | 12.2 | 4.2 | 12 | 19.7 | 9.2 | 11 | 0.02 |
| 23 days treatment | 3.94 | 2.58 | 17 | 14.06 | 10.0 | 11 | 0.001 |

Probiotic supplementation resulted in little difference in Lactobacilli compared to control animals, as measured by both plate and FISH methodology. This finding is unusual in relation to previous findings, when probiotics have been shown to increase the number of beneficial Lactobacilli, and may be due to the compromised health status of the cats in the current study. These cats all had a clinical infection of Campylobacter prior to the beginning of the trial and this would be expected to adversely affect the normal microflora of all cats.

As can be seen, antibiotics decreased the Campylobacter (as a percentage of the total population of fecal bacteria) from 14.38 to 5.69% (P=<0.05, paired T test). At two weeks, Campylobacter levels had risen in both groups, however, the rise in the probiotic+ group was significantly less than in the probiotic− group (12.2 and 19.7% of total population, respectively, P=<0.05). Although the organism count decreased in both groups at four weeks, elimination from the probiotic+ group cats was markedly accelerated (14.06% of total population in probiotic− and 3.94% of total population in probiotic+ cats, P=<0.05).

Probiotic supplementation significantly decreased the levels of potentially pathogenic Campylobacter compared to cats that had received no probiotics.

The study described herein demonstrates that Lactobacillus acidophilus can improve recovery of the feline gastrointestinal tract from the effects of antibiotic therapy, by decreasing the number of Campylobacter as a % of the total population. This would be expected to decrease recovery time of the cat and therefore decrease the zoonotic risk from fecal shedding of Campylobacter.

EXAMPLE 2

Determination of the Anti-Campylobacter Activity of Probiotic Microorganism

Objective

In this study, the ability of potential probiotic strains of bacteria to have an antibacterial effect on Campylobacter jejuni is addressed.

Materials and Methods

Bacterial Strains and Culture Conditions

Campylobacter jejuni cultures were maintained on Mueller Hinton agar (Oxoid) and used as an inoculum for liquid cultures (Mueller Hinton broth, Oxoid) that were grown in 20 ml volumes in 50 ml conical flasks shaken on an orbital shaker.

Potential probiotic strains were maintained on MRS agar and cultured in 20 ml volumes in MRS broth under anaerobic conditions.

Experimental Set-Up
(i) Liquid cultures of probiotic strains were set up and incubated overnight under appropriate conditions. A 1 μl loopful of the overnight culture was then used to inoculate the very centre of a 150 mm MRS agar plate. These large plates were incubated anaerobically overnight to allow the growth from the spot inoculum.
(ii) Pathogenic liquid cultures were set up on the same day as the probiotic spot cultures and incubated overnight. Overnight pathogen cultures were adjusted to $A_{600}$ 0.4 before inclusion in the assay.
(iii) To 15 ml of molten MH agar, 200 μl of the adjusted pathogen culture was added and swirled gently to mix. This agar/pathogen mix was then poured into a 90 mm petri dish and allowed to set.
(iv) When pathogen inoculated agar set it was aseptically removed from the petri dish. Two sterile disposable loops were used to remove the agar by gently lifting it away from the dish and slowly lowering the agar disc onto the spot of probiotic growth on the 150 mm agar plates.
(v) The agar "sandwich" was incubated overnight at 37° C. under aerobic conditions.
(vi) After overnight incubation, the zone of no bacterial growth over the probiotic spot was measured and the diameter of the probiotic spot subtracted from this figure. The resulting value is taken as the zone of inhibition.
(vii) All experiments were carried out a minimum of three times for each strain-pathogen combination.

Results

Anti-Campylobacter Potential of Probiotic Strains

Following incubation of the potential probiotic strains with Campylobacter jejuni the zones of inhibition were determined for each strain (see Table 3 below).

TABLE 3

| Probiotic Strain | Average Inhibition Zone (mm) |
|---|---|
| L. acidophilus | 19.3 |
| L. ruminus | 16.3 |
| L. reuteri | 5.3 |
| L. murinus | 9.3 |
| L. mucosae | 2.7 |
| L. casei | 21.3 |

Discussion

The anti-Campylobacter activity of the strains is clearly demonstrated.

The invention claimed is:

1. A biologically pure culture of a probiotic microorganism, for use in preventing or reducing gastrointestinal Campylobacter infection in a mammalian animal, wherein the probiotic microorganism is Lactobacillus acidophilus having accession number NCIMB 41117.

2. The probiotic microorganism, as claimed in claim 1, which is comprised in a composition.

3. A method for the prevention or reduction of gastrointestinal Campylobacter infection in a mammalian animal, the method comprising feeding said animal a foodstuff having an effective amount of a probiotic microorganism, wherein the probiotic microorganism is Lactobacillus acidophilus having accession number NCIMB 41117.

4. The method, as claimed in claim 3, wherein the foodstuff is a dry pet food.

5. The method, as claimed claim 3, wherein the Campylobacter infection is Campylobacter jejuni.

6. The method, as claimed in claim 3, wherein the animal is a cat, dog or a human.

* * * * *